(12) United States Patent
Bacus et al.

(10) Patent No.: US 6,466,690 B2
(45) Date of Patent: Oct. 15, 2002

(54) METHOD AND APPARATUS FOR PROCESSING AN IMAGE OF A TISSUE SAMPLE MICROARRAY

(75) Inventors: James W. Bacus, Oakbrook, IL (US); James V. Bacus, Downers Grove, IL (US)

(73) Assignee: Bacus Research Laboratories, Inc., Lombard, IL (US)

( * ) Notice: Subject to any disclaimer, the term of this patent is extended or adjusted under 35 U.S.C. 154(b) by 39 days.

(21) Appl. No.: 09/740,711

(22) Filed: Dec. 19, 2000

(65) Prior Publication Data

US 2002/0102011 A1 Aug. 1, 2002

(51) Int. Cl.[7] .................................................. G06K 9/00
(52) U.S. Cl. ....................................................... 382/133
(58) Field of Search ................................. 382/128, 133, 382/134, 282, 284, 305, 306; 128/922; 356/39; 702/21; 348/79

(56) References Cited

U.S. PATENT DOCUMENTS

| | | | | |
|---|---|---|---|---|
| 5,428,690 A | * | 6/1995 | Bacus et al. ................. | 382/133 |
| 5,793,969 A | * | 8/1998 | Kamentsky et al. ... | 395/200.43 |
| 6,031,930 A | * | 2/2000 | Bacus et al. ................. | 382/133 |
| 6,101,265 A | * | 8/2000 | Bacus et al. ................. | 382/128 |
| 6,137,897 A | * | 10/2000 | Emi et al. .................... | 382/128 |
| 6,362,004 B1 | * | 3/2002 | Noblett ......................... | 436/43 |
| 6,362,832 B1 | * | 3/2002 | Stephan et al. .............. | 345/629 |

* cited by examiner

Primary Examiner—Andrew W. Johns
(74) Attorney, Agent, or Firm—Fitch, Even, Tabin & Flannery

(57) ABSTRACT

A method and apparatus for processing an image of a tissue sample microarray include placing a plurality of tissue samples in an array on a microscope slide. The tissue samples are then simultaneously and uniformly treated, as by staining. Images of the tissue making up the microarray are captured and stored together with identifying information related thereto. The images may be displayed from the digital storage medium using a programmed processor which can select various magnifications for display. The images also can be accessed by network and remotely.

15 Claims, 9 Drawing Sheets

METHOD AND APPARATUS FOR PROCESSING AN IMAGE OF A TISSUE SAMPLE MICROARRAY

BACKGROUND OF THE INVENTION

The invention relates in general to a method and apparatus for processing images of a tissue sample microarray made up of a plurality of tissue microarray dots using an optical microscope. More particularly, the invention relates to a method and apparatus for capturing tissue sample images from the tissue sample microarray, indexing such images and manipulating and transmitting them.

It is known that in the treatment and prevention of cancers it is often important periodically to examine persons at risk for cancer. In some instances it may be necessary to biopsy tissue from such persons. As medical care has become available to more people and as the need for such increased vigilance has been recognized, the number of biopsies has increased.

One of the problems with evaluating biopsy materials is that in most cases microscopic evaluation of cellular structure and tissue architecture has been important in making determinations as to whether cellular changes have occurred in tissues indicative of cancer or whether cancer is actually present. In the past, such determinations have been made by employing microscopic examinations of tissues and associated cellular structures.

A number of techniques have been developed, including techniques developed by the present inventors, for providing greater accuracy and throughput for such biopsy systems.

In one such system tissues from a particular patient which have been stained are positioned from a particular patient on a microscope slide and are imaged by a light microscope. The images are captured and digitized in a tiled format. The tiles can be reassembled substantially in real time to create pan and scan images of large amounts of tissue at high magnification while simultaneously providing a second digitized image of tissue at low magnification to provide a guide to regions of interest of the pathologist. This system has proven to be a boon to pathologists.

Improvements made upon that system, such as that disclosed in U.S. Pat. No. 6,031,930 to Bacus et al., are directed to further enhancements of the microscopic image examination in that detailed features of the morphometry of images of microscopic objects, such as cells, cell fragments, and the like, are made more easy. Statistical measures are applied which are highly discriminating for neoplasia across diverse tissue types, such as breast, colon, cancer, cervical tissue, and the like. In addition, such systems are valuable in providing assaying functions for different carcinogens and chemopreventive agents.

More specifically, such systems use microscopic images of stained neoplastic tissue sections which are microscopically scanned to provide electronic or digitally recorded. Morphometric features of tissue sample images are measured in first unit values and texture measurements of the tissue samples, such as a Markovian texture measurement, are also made. The respective results are recorded on a grading common scale so that progression of cancer can be ascertained relative to normal tissue.

An additional advance has been made, as exemplified by U.S. Pat. No. 6,101,265 to Bacus et al. Bacus et al. disclose the use of an imaging system which can scan stained tissue samples on microscope slides and generate tiled images thereof. The system also provides low and high magnification image pan and scan capability both locally and remotely. Typical magnifications are 1.25 power, 4 power, 20 power, and 40 power. This allows a pathologist at a remote site to be able to examine a complete and accurate magnified record of the tissue. This can occur over a packet network, such as the Internet or the like, without the need for a wide-band, high-speed transmission, such as a television line.

Despite each of the advantages which have been provided by the previous systems, they still have some drawbacks when presented with newer technologies for rapid assay of large amounts of tissue. Recently, molecular profiling of tissue specimens has come into wider use. This process has to do with the discovery of new genes and targeting genetic probes for attachment to particular tissue regions and molecules such as epitopes. Pharmaceutical companies and researchers in the biological sciences are interested in developing antibody-based probes using standard antibody staining reactions in order to detect molecular abnormalities on the surfaces of cells.

In order to assay such wide collections of patients, it is necessary to collect large amounts of data from the patients. It is known to prepare tissue sample microarrays which consist of a plurality of circular sections of tissue drawn from a variety of persons or sampling sites and placed on a single microscope slide. Such samples are prepared by taking a very small diameter punch, removing punch cores of tissue and placing them into open columns in a paraffin block which open columns are arranged in a grid type array which may for instance have two to three hundred columns available. The total size of the block is small enough that an end section of the block would conveniently fit on a microscope slide under a cover glass or cover slip. Once the columns of tissue are placed within the block, the block is further treated so that the paraffin invades the tissue to provide a typical paraffin biological specimen. The block may be sectioned using separate microtome sectioning techniques and the sections with the two to three hundred circular tissue sample "dots" may be placed on a microscope slide.

The slide may be subjected to staining and other antibody treatment and has the particular advantage that all two to three hundred of the specimens in the microarray are subjected to simultaneous and identical staining conditions, temperature conditions, and the like, so that variables need not be controlled for between patients who are being examined and a standardized treatment as applied to the tissue.

One of the problems, however, with such microarray-based assays is that the slides must be processed by hand. A microscopic determination must be made of characteristics of each of the tissue samples. At times tissue dots may fall off the slides opening up voids in the array or grid. It is easy for researchers who are examining the slides to lose track of which piece of tissue is being examined.

Although the microarray staining techniques have provided a considerable advantage in speeding up molecular assaying, the analysis of such results continues to be time-consuming and may be subject to more increased error than other types of assay systems.

What is needed then is a system which would provide for rapid assay of a microarray by an operator so that the advantages of bulk microarray treatment techniques can be fully realized.

SUMMARY OF THE INVENTION

A method and apparatus for processing an image of a tissue sample microarray include placing a plurality of tissue samples in an array or a rectangular grid on a conventional glass microscope slide. The tissue samples, which have been sectioned and form the array, may then be treated simultaneously as by staining the entire slide with a suitable biological stain for providing contrast to image various structures within the tissues or cells making up the multiple samples of the microarray. The advantage of doing this is that it allows multiple samples taking from multiple patients to be treated in substantially the same way and reduces the number of controls which must be put in place during the experiment.

The tissue sample microarray is prepared by taking a core or "punch" of tissue from a tissue sample the core may have a diameter of a millimeter or less and the cored tissue is inserted into an open channel which is a right circular cylinder channel which is one of a rectangular array of channels formed in a paraffin block. The paraffin block is then treated so that the paraffin enters the tissue which is placed into each of the channels. The block may then be sectioned by a microtome as are other parafin block tissue samples. The microtome section may then be lifted and then placed on a microscope slide in a conventional manner. In this manner one or more microarrays may be placed on a single microscope slide. The microarrays typically have two to three hundred dots of tissue thereon, there may be up to six microarrays on a slide for over one thousand tissue samples on the slide which are subjected to substantially the same staining treatment. After staining, washing and the like are completed a cover slip is placed on the slide to make the slide permanent.

The slide may be placed on a movable stage of a scanning microscope. The microscope allows the user to take a low magnification image of a plurality of tissue dots in the microarray grid. The user may then identify corners of a scanned pattern. The scan pattern is usually rectangular and encompasses a subset of the tissue dots which are to be scanned.

An imager, optically connected to receive images from the microscope, generates a digital image which is fed to a processor and displayed on a display. The displayed image identifies the four corners of the grid to be scanned. It then shows target points at what would be expected to be the center points of the tissue dots in the grid array. Sometimes the dots are not precisely registered with uniform center-to-center distances within the array. Some tissue dots even may be missing. The user is then prompted with a cross-hair in each of the dots. Through the use of a mouse-select and drag operation the user can re-center the dot center point for the scan within each dot.

Once this has been done tiling grids are constructed and displayed over each of the images of the selected tissue dots. The tiling grids may typically include three rows and three columns of rectangular image tiles per tissue dot image. Tiling does not take place in the substantially empty or dot-free portions of the microarray.

The user may then command the computer to tile at least a portion of the dot images in the microarray. This consists of the microscope stage receiving commands at its X and Y stepper motors and then moving its stage and the slide it carries to a first position in a particular tile grid array of a selected dot image. A first dot image tile is captured. The stage is moved to the next tile position for that tissue dot and the next tile image is captured. In this manner all of the high magnification tile images at 20 to 40 power for that particular dot are captured. After completion of the capture of the first set of tile images for that dot additional capture takes place at successive tissue dots until the tiled images of all tissue dots within the selected tissue dot sub-array are captured.

After the dot images are captured data structures are set up associating block identification, user identification and patient identification with each of the tiled dot images. The specific identifying information at the block, user and patient levels may be inserted by the operator of the microscope at the time of dot image capture or later. In this way the tiled tissue dot microarray images are directly associated with the tissue dots in storage so that even if the original tissue microarray slide is lost the visual information and identifying information associated with the project would not be lost.

It is a principal aspect of the present invention to provide an image processing system which rapidly and completely scans and captures low magnification and high magnification images of a microarray of tissue specimens.

It is another aspect of the present invention to provide a method and apparatus for associating each of the images of the tissue samples or tissue dots within the microarray with a unique identifier so that the dot images can later be identified and accessed and be quickly and easily evaluated.

Other aspects and advantages of the present invention will become obvious to one of ordinary skill in the art upon appraisal of the remainder of the specification in light of the accompanying drawings and claims.

DETAILED DESCRIPTION OF THE PREFERRED EMBODIMENT

Figure 1:
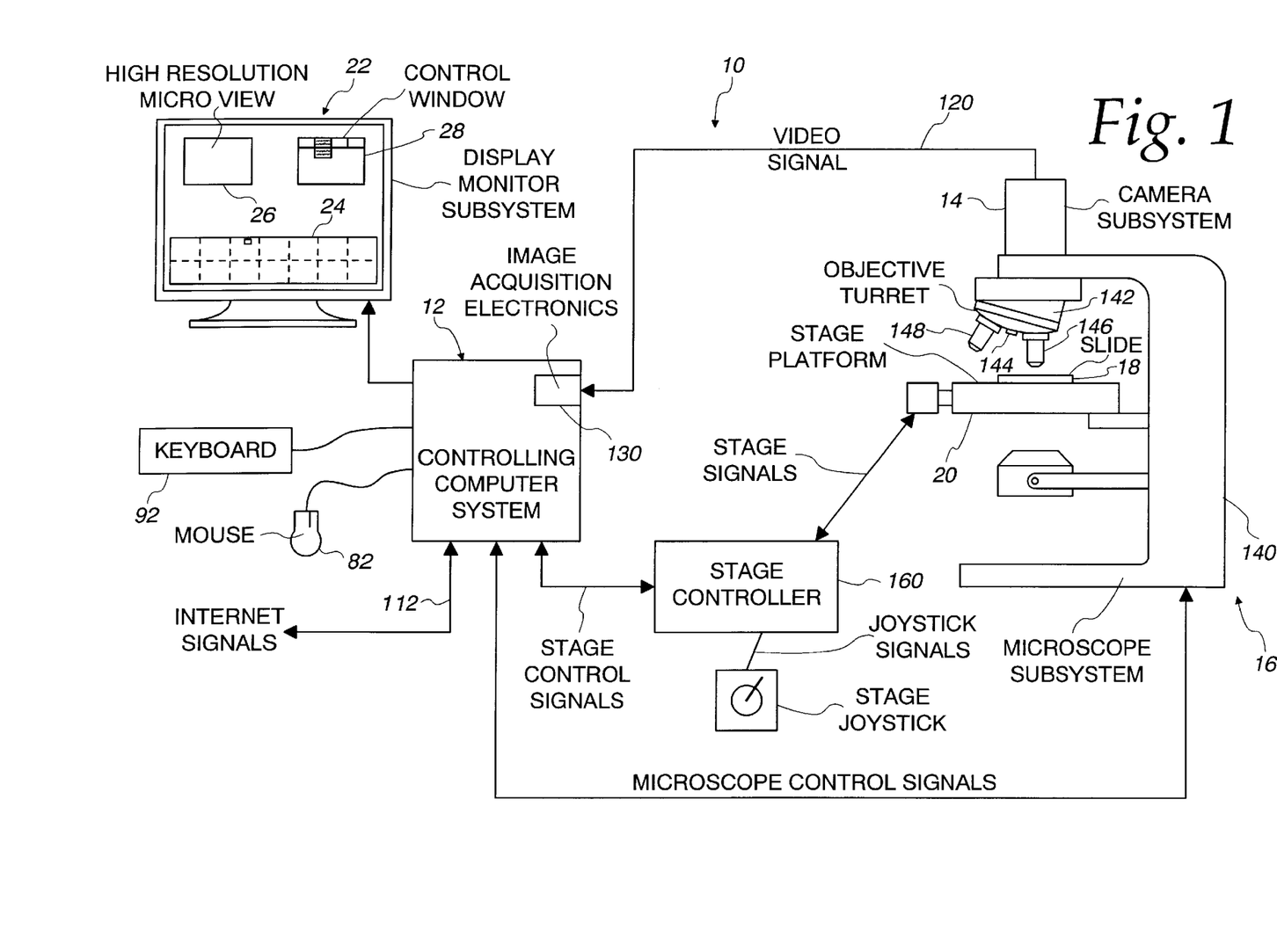
FIG. 1 is a block diagram of an apparatus embodying the present invention.

Referring now to the drawings and especially to FIG. 1, an apparatus embodying the present invention is shown therein and generally identified by reference numeral 10. The apparatus 10 is adapted for synthesizing low magnification and high magnification microscopic images of tissue sample microarrays. The apparatus 10 includes a computer 12 which is a dual microprocessor personal computer in combination with a Hitachi HV-C20 video camera 14 associated with a Zeiss Axioplan 2 microscope 16. The computer system 12 receives signals from the camera 14 which captures light from the microscope 16 having a microscope slide 18 positioned on an LUDL encoded motorized stage 20. The encoded motorized stage 20 includes a MAC 2000 stage controller for controlling the stage in response to the computer 12.

A microscope slide 18 includes a plurality of tissue sample microarrays 19 each comprising a tissue sample microarray made up of a grid or array of circular tissue sample sections or dots 21, which are to be viewed by the microscope and whose images are to be digitized both at low magnification and at high magnification as selected by a user. The low magnification digitized image is then displayed on a 21 inch Iiyama video display monitor 22 having resolution of 1600 by 1200 to provide display screens of the type shown in FIG. 1 including a high magnification image 26, for instance at 40 power and a control window or image 28. A low magnification image may also be generated separately or simultaneously on the screen so that a pathologist or other operator of the system can review architectural regions of interest in low magnification and simultaneously view them in high magnification in the high magnification screen or window 26 to determine whether the cells forming a portion of the architectural feature need be examined further for cancer or the like or not.

Figure 2A:
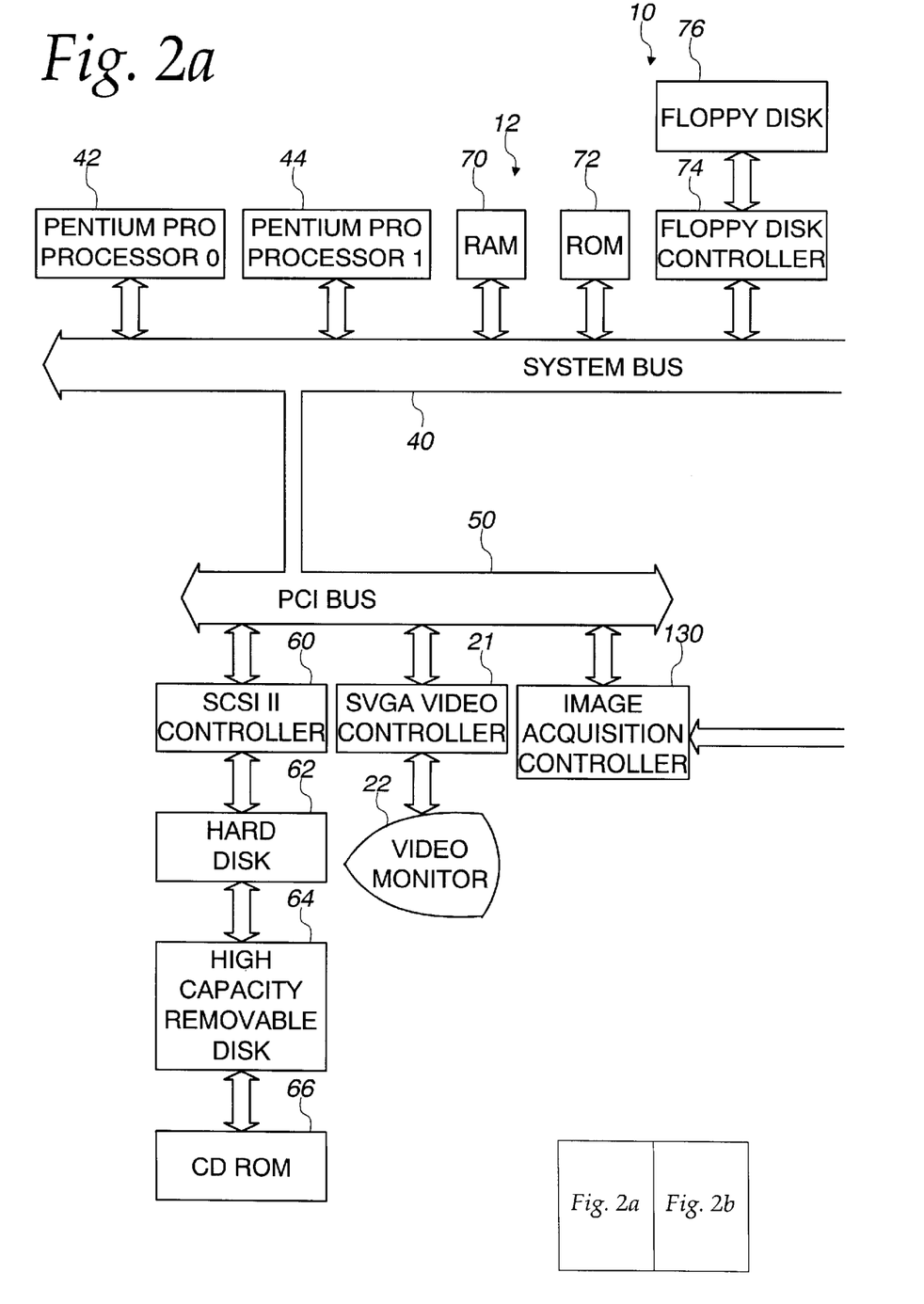
FIGS. 2A and 2B are block diagrams of a portion of the apparatus shown in FIG. 1.
Figure 2B:
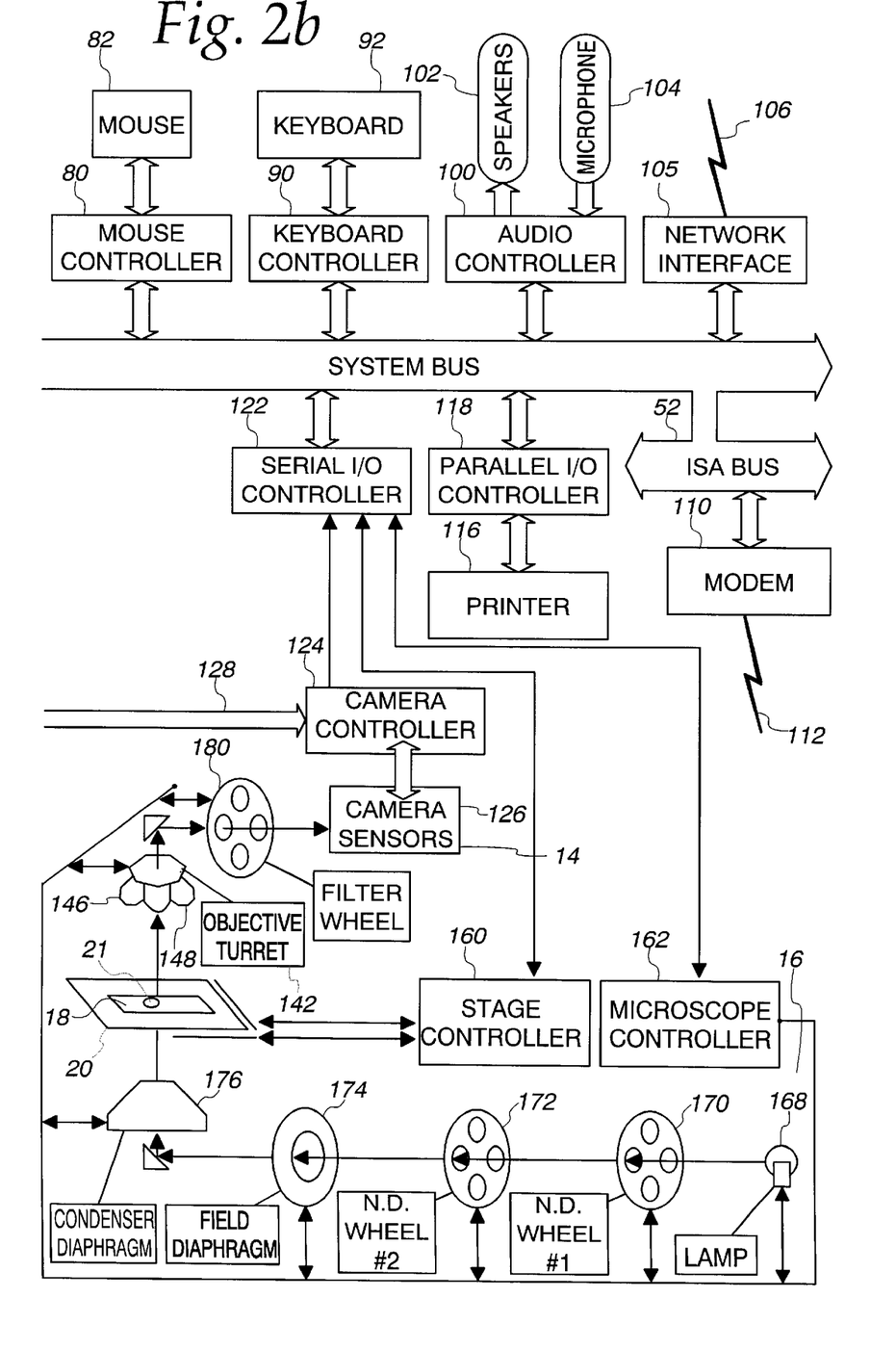

The computer 10 is constructed around a PCI system bus 40 although other bus structures such ATX may be used. A first microprocessor 42 and a second microprocessor 44 are connected thereto. The microprocessors may be Pentium III or the like high performance microprocesors. The system bus 40 has connected to it a PCI bus 50 and an ISA bus 52. The PCI bus 50 has a SCSI controller 60 connected thereto to send and receive information from a hard disk 62. The hard disk 62 also is coupled in daisy-chained SCSI fashion to a high capacity removal disk and to a CD-ROM drive 66. The hard disk 62 contains the programs for operating the system for controlling the microscope 16 and for processing the images as well as for performing a quantitative analysis of the selected portions of the tissue sample microarrays 19 being viewed on the slide 18.

The system bus 40 also has connected to it a random access memory (RAM) 70 within which portions of the program being executed are stored as well as a read only memory (ROM) 72 for holding a bootstrap loader and portions of a basic input/output operating system. A floppy disk controller 74 is coupled to the system bus 40 and has connected to it a floppy disk drive 76 for reading and writing information to a floppy disk as appropriate.

A mouse controller 80 is coupled to the system bus 40 and has a mouse 82 which operates as a pointing device for controlling manipulations on the screen 22 and within the windows 24, 26 and 28. A keyboard controller 90 is connected to the system bus 40 and has a keyboard 92 connected thereto. The keyboard 92 may be used to send and receive alphanumeric signals and control signals to other portions of the computer.

An audio controller 100 has a plurality of speakers 102 and a microphone 104 connected thereto for audio input and output and is coupled to the system bus 40. A network interface, such as a network interface card 104, is connected to the system bus 40 and can provide signals via a channel 106 to other portions of a network or the Internet to which the system may be connected. Likewise, signals can be sent out of the system through a modem 110 connected to the ISA bus 52 and may be sent via a channel 112, for instance, to the Internet. A printer 116 is connected via a parallel I/O controller 118 to the system bus 40 in order to provide printouts, as appropriate, of screens and other information as they are generated. A serial I/O controller 122 is connected to the system bus 40 and has connected to it a camera controller 124 which is coupled to CCD sensors 126 in the cameras. The CCD sensors 126 supply pixel or image signals representative of what is found on the slide 18 to an Epix pixci image acquisition controller 130 coupled to the PCI bus 50.

The microscope 16 includes a base 140 having a stage 20 positioned thereon as well as an objective turret 142 having a plurality of objectives 144, 146 and 148 thereon. The objective 144, for instance, may be of 1.25× objective. The objective 146 may be a 20X objective. The objective 148 may be a 40X objective. Signals from the CCD sensors 126 and controller are supplied over a bus 128 to the image acquisition system where they are digitized and supplied to the PCI bus for storage in RAM or for backing storage on the hard disk 62.

Figures 3, 4:
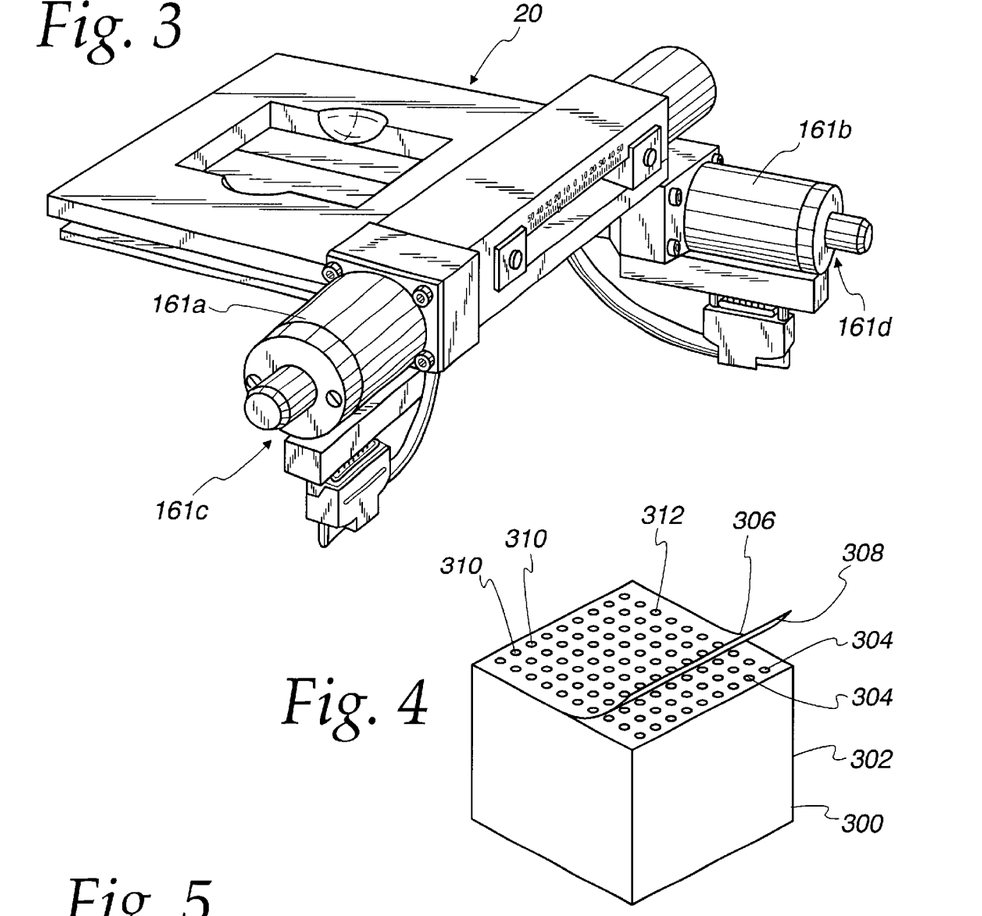
FIG. 3 is a perspective view of a microscope stage assembly including stepper motors for moving a slide-holding stage, and shaft encoders for indicating stage position and providing a closed loop drive for the stepper motors.
FIG. 4 is a perspective of a microarray slice being separated from a tissue sample paraffin block containing a plurality of plugs of tissue.

When a tissue sample microarray 19 is on the slide 18 the stage 20 may be manipulated under the control of the computer through a stage controller 160 coupled to the serial I/O controller 122. The stage controller sends motion commands to a pair of stepper motors 161a and 161b. A pair of shaft encoders 161c and 161d send stage position signals back. Likewise, a microscope controller 162 controls operating characteristics of the microscope 16 such as illumination, color temperature or spectral output of a lamp 168 and the like. For instance, in normal operation, when a tissue sample microarray slide 18 is placed on the stage 20, as shown in FIG. 1, the processors 42 or 44 send a command through the system bus to cause the serial I/O controller 122 to signal the microscope controller to change magnification to 1.25× in a step 202. This is done by rotating the objective turret of the Axioplan 2 microscope to select the objective 144. Likewise, the controller sets the color temperature of the lamp 168, sets a pair of neutral density filter wheels 170 and 172 and sets a field diaphragm 174 for the correct illumination. A condenser diaphragm 176 is also controlled. A color filter wheel 180 may also be controlled to apply the appropriate filter color to the CCD sensors 126 in the camera.

In order to provide a magnification called for in, the overall illumination and control of the microscope will be controlled so that the objective turret 142 will to be rotated to place the higher power objective above the slide 18. The voltage to the lamp will be changed to adjust the lamp 168 to provide the proper illumination and color temperature as predetermined for the selected objective. The condenser diaphragm 176 will have its opening selected as appropriate to provide the proper illumination for that objective.

The filter turret 180 will select the proper light wavelength filter to be supplied to the camera sensors. For instance, a red, blue, or green filter, as appropriate, particularly if the specimen has been stained. The field diaphragm 174 will have its opening changed. The neutral density filter wheel 170 will select a neutral density filter and the neutral density filter wheel 172 will also select a neutral density filter. The X, Y and Z offsets will be used for reconstruction of the recorded image at the selected magnification. The current stage or slide position will be read from encoders in the stage which are accurate to 0.10 micron.

A substantially rectangular paraffin block 300 comprised of a substantially rectangular section of paraffin 302 has a plurality of columns of tissue 304 embedded therein and extending substantially through the block to form a block microarray. A section 306 is shown as being partially removed from the block as by a microtome (not shown). The section 306 comprises a layer of parafin 308 having a plurality of tissue dots 310 formed in rows and columns to define a substantially rectangular microarray 312.

Figure 5:
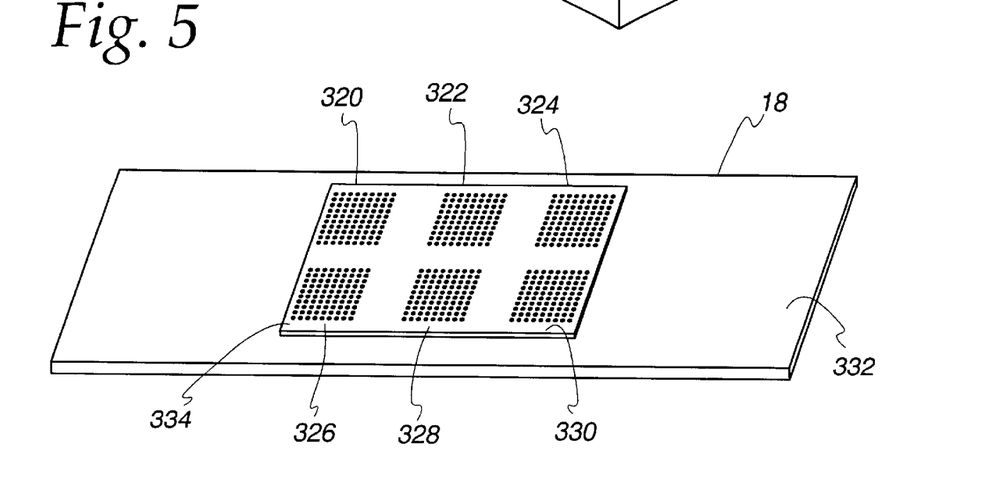
FIG. 5 is a perspective view of a microscope slide carrying multiple microarrays.

It may be appreciated that one or more of these arrays may be placed on the slide 18 as is shown in FIG. 5. A plurality of microarrays, respectively numbered 320, 322, 324, 326, 328 and 330, is placed on a surface 332 of the slide 18 under a conventional cover slip 334. The microarrays are obtained from sections of paraffin blocks of the type shown in FIG. 4 and are placed on the slide 18. The slide 18 is then treated by staining or exposing it to molecular probes. All of the tissue dots in each of the microarrays 320–330 are uniformly treated and exposed to the stain thus controlling for what would otherwise amount to staining differences from slide to slide.

Figure 6:
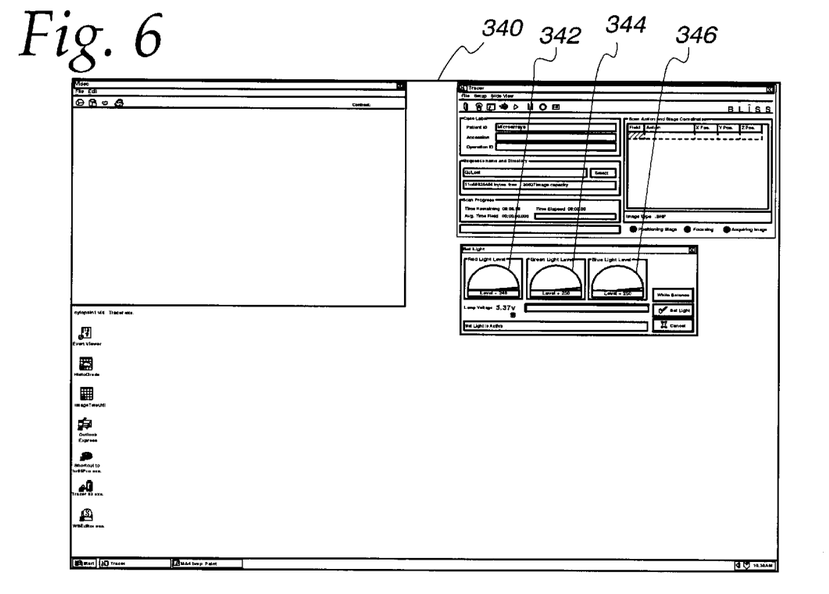
FIG. 6 is a view of a set-up screen for setting the red, green, and blue light levels for a scanning microscope shown in FIG. 1.

The slide 18 is then placed on a stage of the microscope. The microscope has its light level adjusted through the use of a dialog box. As may best be seen in FIG. 6 a dialog box 340 shows a red light level indication 342, a green light level indication 334, and a blue light level indication 346. The light level may be adjusted prior to scanning the microarray.

Figure 7:
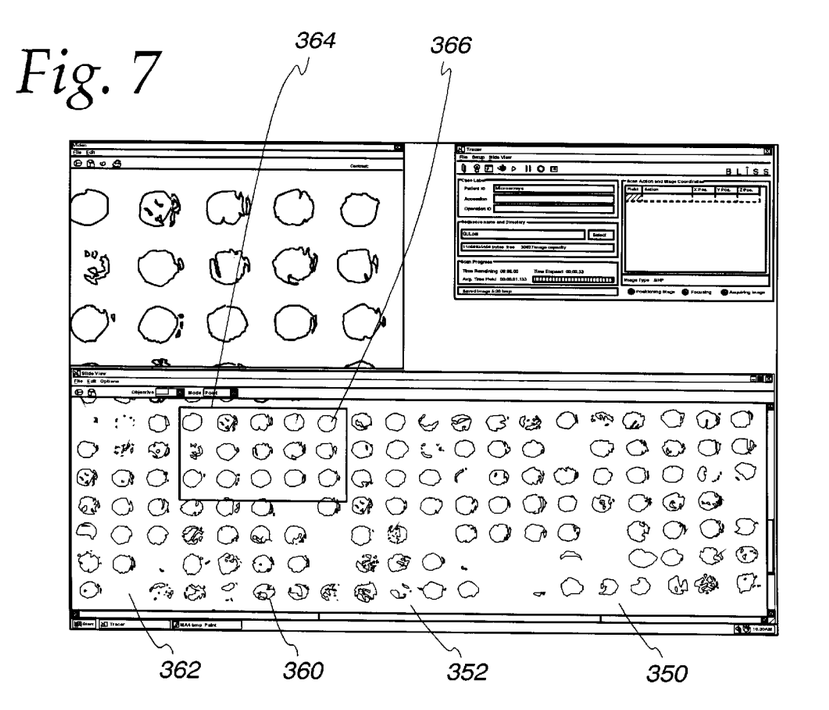
FIG. 7 is a view showing the selection of a subset of the dots in a microarray to be scanned for the apparatus shown in FIG. 1.

The microarray may be initially at low power scanned and a scanned relatively low magnification image 350 stored in the computer memory and displayed in a window 352, as shown in FIG. 7. In order to determine greater detail of a plurality of tissue dots 360 in a microarray 362 a boundary may be defined around the dots as shown by the rectangular boundary 364 by doing a click and drag operation using the mouse. The tissue dots 366 shown within the rectangular region 364 are then selected to be scanned at high magnification.

Figure 8:
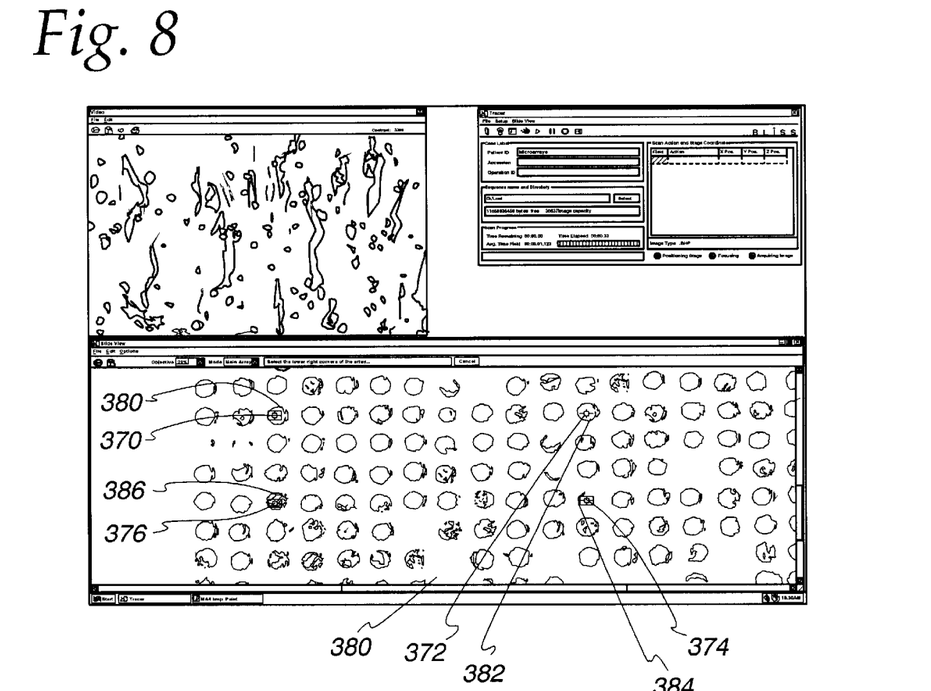
FIG. 8 is a screen shot for a dot scan path configuration for the apparatus shown in FIG. 1.

As may best be seen in FIG. 8 a plurality of corner points 370, 372, 374, and 376 are shown in the low magnification dot array window 330. The corner points are initially positioned near the centers of respective tissue dots 380, 382, 384 and 386. On the basis of the selection of those corner points the system then generates center points for each of the tissue dots assumed to be within the array region.

Figure 9:
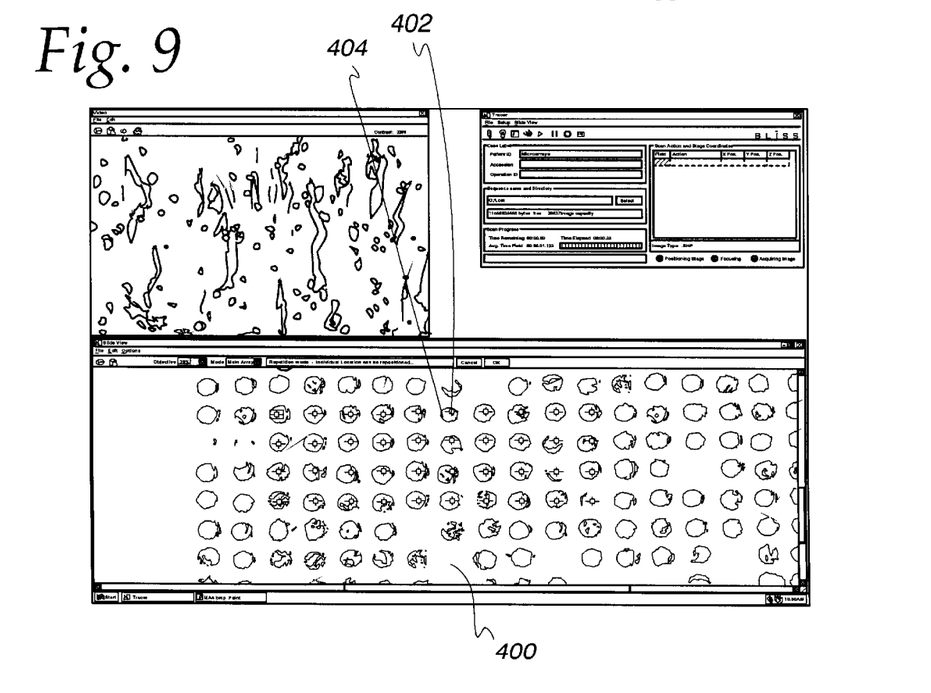
FIG. 9 is a screen shot showing a method of repositioning the areas to be scanned in registration with the actual images of the tissue array dots for the apparatus shown in FIG. 1.

As may best be seen in FIG. 9 and as shown in the window 400, the center points are shown with cross-hairs and blocks as the exemplary center point 402 is shown within a tissue dot 404. Since it may be appreciated that the preselected center points may not be strictly in registration with the tissue dots the operator of the system may click and drag the center point within a dot and recenter it prior to allowing the dot to be scanned at high magnification.

Figure 10:
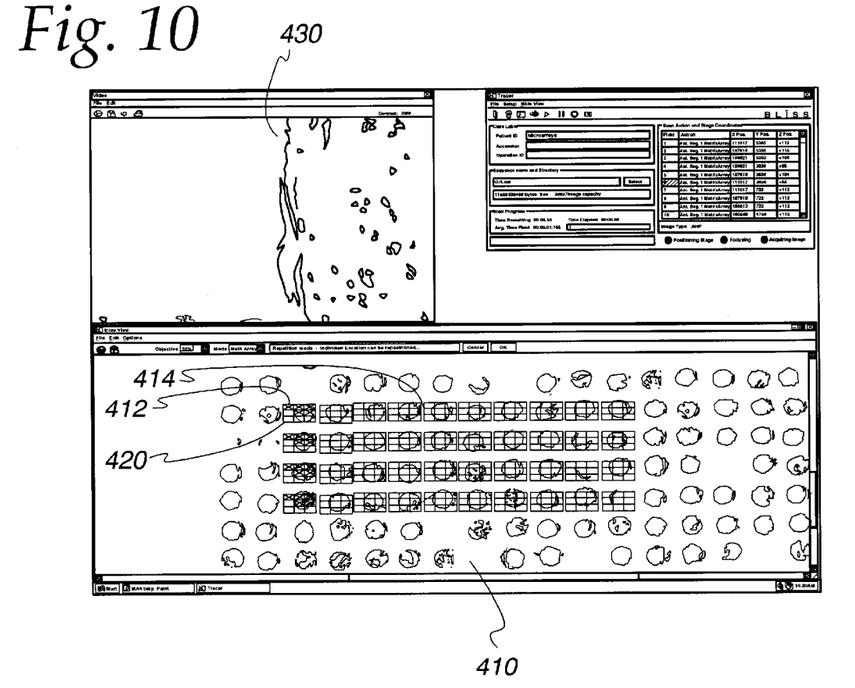
FIG. 10 is a screen shot showing a gridding system having been set up on a tissue dot-by-tissue dot basis, and the beginning of a scan occurring on a 3×3 image tile grid covering an upper, left-hand dot, and a 4×10 array of dots with five of the image tiles having been filled or scanned for the first tissue dot for the apparatus shown in FIG. 1.

The results of such a recentering may best be seen in FIG. 10 wherein a low magnification window 410 having a plurality of dots also has 3×3 tiled grids 412 formed thereover. It may be appreciated that the tile grids are not strictly in registration or in contact with one another as there are open spaces 414 positioned therebetween. However, each of the tiled grids completely covers the individual dot image which is to be tiled or scanned. A scan pattern is set up moving back and forth across the 3×3 rows and columns as may best be seen for the tile grid 412 wherein five of the nine tiles are shown with X's formed therein and indicating that those tiles have already been scanned. The next tile to be scanned is shown in magnified form in a high magnification window 430 shown on the screen.

Figure 11:
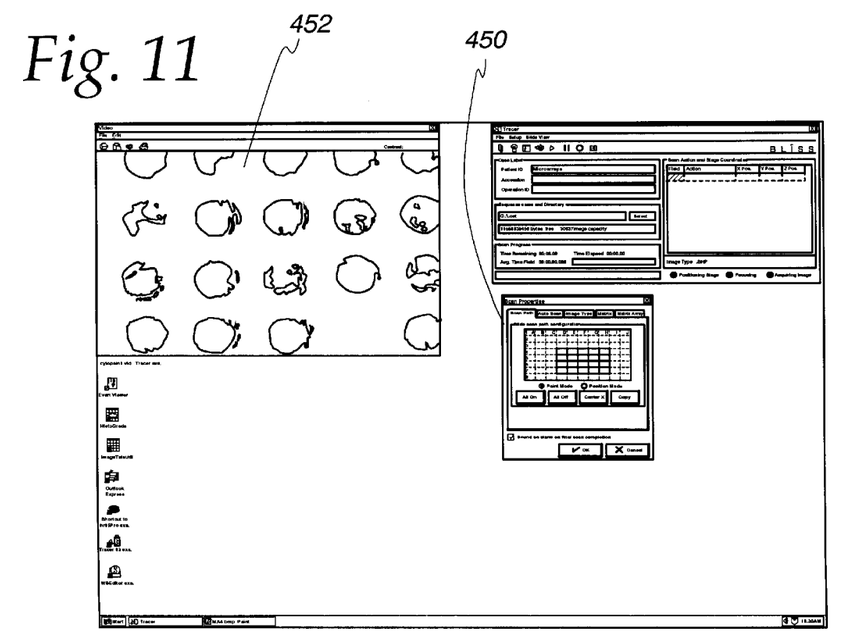
FIG. 11 is a screen shot showing a magnified view of the tiled dot images after having been scanned for the apparatus shown in FIG. 1.

Subsequent to scanning or before scanning, slide scan paths may be changed or reconfigured as shown by a dialog box 450 shown in FIG. 11 along with a low magnification window 452 of a portion of a microarray.

Figure 12:
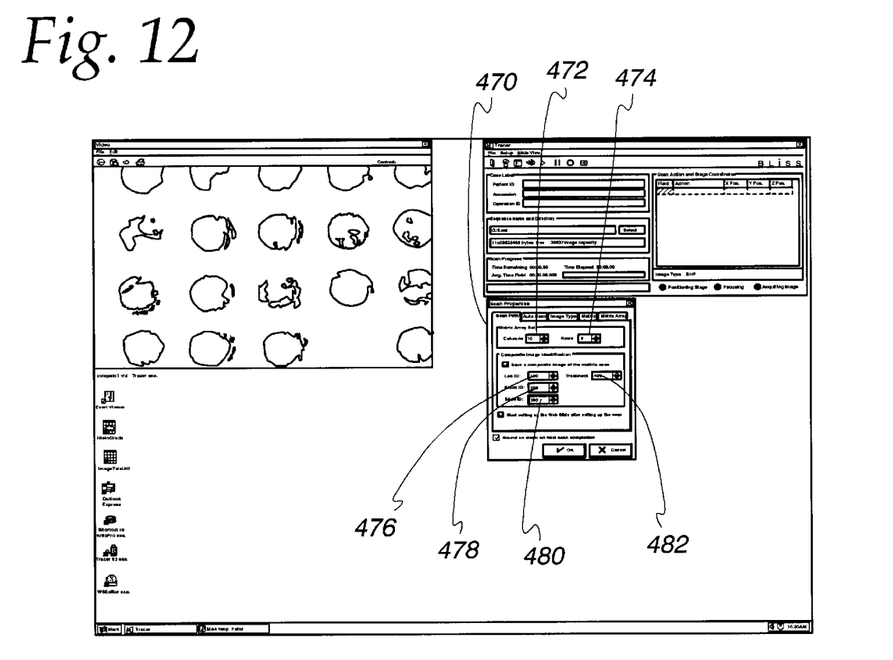
FIG. 12 is a magnified view of the dot images after having been scanned showing the addition of a lab ID, a block ID, and a slide ID for the apparatus shown in FIG. 1.

Also subsequent to scanning the tiled images and assembled into seamless tiled images of the dots for display including panning and scanning. Each of the dots in the matrix array is selected by a dialog box 470 which identifies the dot in the matrix array by column number 472, row number 474, and then assigns a lab ID 476, a block ID 478, a slide ID 480 and a treatment ID 482 to the dot. Patient ID's may also be assigned. These identifications are then associated with the dot image as it is stored on the hard disk drive in both low magnification tiled format and high magnification tiled format image format.

Figure 13:
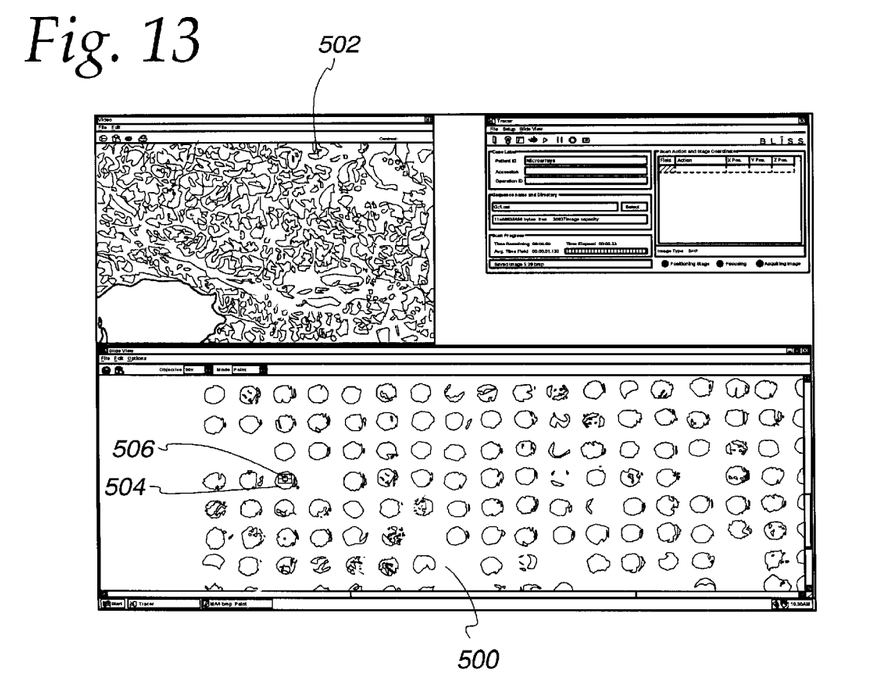
FIG. 13 is a view showing a selected portion identified by a rectangular boundary of one of the dots from the dot image and a magnified view of the bounded region at 20 power for the apparatus shown in FIG. 1.
Figure 14:
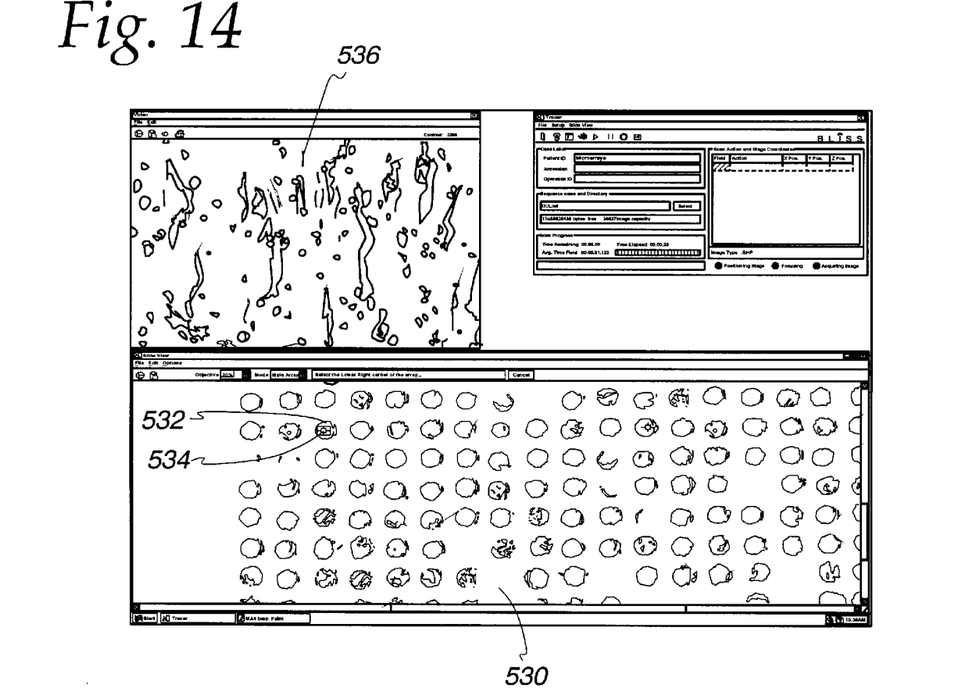
FIG. 14 is a set-up array for a series of dots showing a portion of the tissue from one dot at 20 power magnification for the apparatus shown in FIG. 1.

Low magnification and high magnification display of portions of the microarray may be carried out in a low magnification window 500 and a high magnification simultaneous window 502 as shown in FIG. 13. The high magnification window 502 is selected from a dot 504 by a high magnification window select region or rectangle 506 placed thereover. In this case the high magnification window 502 shows a 20-power magnification of a stained tissue sample such as from a breast cancer or the like. High magnification windows may also be identified as shown in FIG. 14 where in a low magnification window 530 the dot array has a dot 532 with a high magnification identification box or rectangle 534 identified therein. The high magnification or 20-power view of the tissue is shown in window 536.

Figure 15:
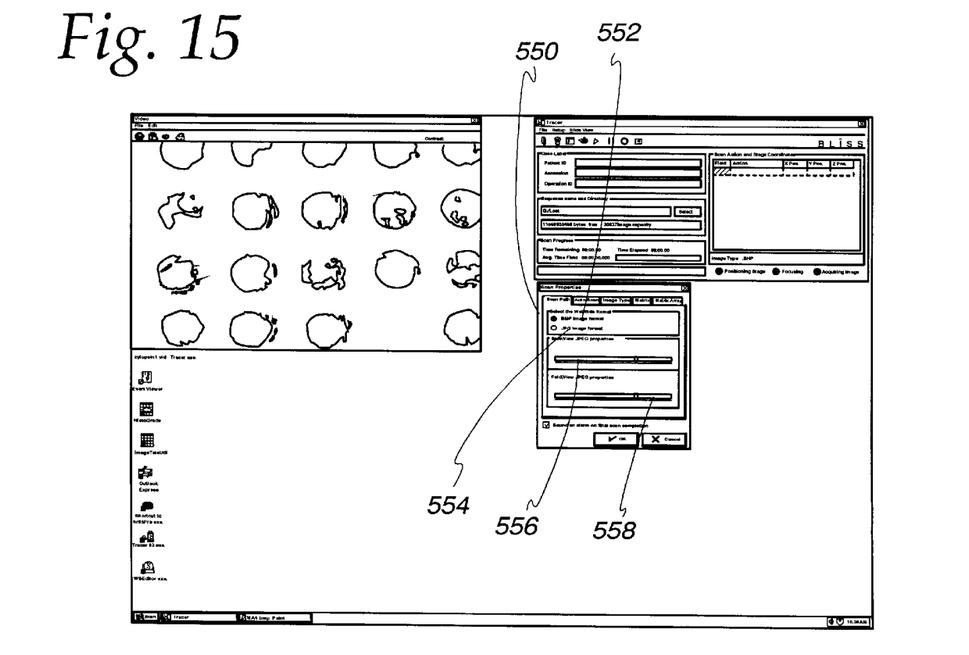
FIG. 15 is a view of a portion of the microarray dots wherein an uncompressed or BMP image format has been selected but also providing the ability to select a compressed or JPEG image format including selection of slide-view JPEG properties and field-view JPEG properties for the apparatus shown in FIG. 1.

The dot images may be stored in compressed or uncompressed format. A dialog box is provided to the user as shown in FIG. 15. The dialog box 550 allows the user to select uncompressed BMP image format 552 or compressed JPEG image format 554. In addition the amount of compression of the slide view 556 and for the field view 558 are user selectable by dialog box slides.

It may be appreciated then that the instant invention provides a convenient and rapid way to analyze and identify hundreds or thousands of microarray tissue samples quickly and conveniently during a molecular assay study.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed is:

1. A method of processing an image of a tissue sample microarray, comprising:

placing a plurality of tissue samples in an array on a microscope slide;

treating simultaneously all of the tissue samples on the microscope slide with a substantially identical treatment;

scanning each of the tissue samples and generating image signals representative thereof;

storing the tissue sample image signals;

indexing stored images of the tissue samples.

2. A method of processing an image of a tissue sample microarray according to claim 1, wherein the tissue samples comprise microarray tissue sample dots.

3. A method of processing an image of a tissue sample microarray according to claim 2, further comprising:

retrieving a stored image of at least a portion of one of the dots; and displaying the stored image.

4. A method of processing an image of a tissue sample microarray according to claim 3, wherein the displayed image is a low magnification image of a dot.

5. A method of processing an image of a tissue sample microarray according to claim 3, wherein the displayed image is a high magnification image of at least a portion of one of the tissue dots.

6. A method of processing an image of a tissue sample microarray according to claim 2, wherein scanning the microarray dots further comprises generating a plurality of image tiles and combining the image tiles into a dot image.

7. A method of processing an image of a tissue sample microarray according to claim 2, wherein the treatment comprises staining the plurality of tissue samples in the array on the microscope slide.

8. A method of processing an image of a tissue sample microarray according to claim 2, further comprising providing an output indication of a dot characteristic in a text format.

9. A method of processing an image of a tissue sample microarray according to claim 2, further comprising:

generating a tentative dot grid array; and providing a prompt to an operator to provide a command to align an element of a dot grid array scan area.

10. A method of processing images of a tissue microarray, comprising:

selecting at least a portion of a tissue sample image from a tissue image set of a stored microarray file which was generated from multiple tissue samples on a microscope slide simultaneously subjected to a substantially identical treatment, the stored microarray file including identifying information individualized for each of the stored tissue sample image sets; and displaying at least a portion of the stored tissue image.

11. A method of processing images of a tissue image microarray according to claim 10, wherein the tissue image sets are dot images.

12. A method of processing images of a tissue image microarray according to claim 11, wherein the portion of the stored tissue image is displayed remotely.

13. A method of processing images of a tissue image microarray according to claim 11, wherein the displayed image is manipulated remotely.

14. A method of processing images of a tissue image microarray according to claim 11, wherein the displayed image is a low magnification image.

15. A method of processing images of a tissue image microarray according to claim 11, wherein the displayed image is a high magnification image.

* * * * *

US006466690C1

(12) INTER PARTES REEXAMINATION CERTIFICATE (0039th)
United States Patent
Bacus et al.

(10) Number: US 6,466,690 C1
(45) Certificate Issued: Nov. 18, 2008

(54) METHOD AND APPARATUS FOR PROCESSING AN IMAGE OF A TISSUE SAMPLE MICROARRAY

(75) Inventors: James W. Bacus, Oakbrook, IL (US); James V. Bacus, Downers Grove, IL (US)

(73) Assignee: Bacus Laboratories, Inc., Lombard, IL (US)

Reexamination Request:
No. 95/000,014, May 16, 2003

Reexamination Certificate for:
Patent No.: 6,466,690
Issued: Oct. 15, 2002
Appl. No.: 09/740,711
Filed: Dec. 19, 2000

(51) Int. Cl.
*G06K 9/00* (2006.01)

(52) U.S. Cl. ........................................... 382/133
(58) Field of Classification Search ................... None
See application file for complete search history.

(56) References Cited

U.S. PATENT DOCUMENTS

| | | | | |
|---|---|---|---|---|
| 4,741,043 | A | | 4/1988 | Bacus ........................ 382/129 |
| 4,777,525 | A | | 10/1988 | Preston, Jr. ................. 358/102 |
| 4,820,504 | A | | 4/1989 | Battifora ........................ 424/3 |
| 4,914,022 | A | | 4/1990 | Furmanski et al. ............. 435/7 |
| 5,428,690 | A | | 6/1995 | Bacus et al. ................. 382/128 |
| 5,836,877 | A | | 11/1998 | Zavislan ..................... 600/407 |
| 5,989,835 | A | * | 11/1999 | Dunlay et al. ................ 435/7.2 |
| 6,004,755 | A | | 12/1999 | Wang ............................. 435/6 |
| 6,103,479 | A | * | 8/2000 | Taylor ........................ 435/7.2 |
| 6,349,144 | B1 | * | 2/2002 | Shams ........................ 382/129 |
| 6,430,309 | B1 | | 8/2002 | Pressman et al. ............ 382/133 |
| 2002/0132246 | A1 | | 9/2002 | Kallioniemi et al. ........... 435/6 |
| 2002/0168639 | A1 | * | 11/2002 | Muraca .......................... 435/6 |
| 2002/0192702 | A1 | | 12/2002 | Kononen et al. ............... 435/6 |
| 2003/0138827 | A1 | | 7/2003 | Kononen et al. ............... 435/6 |

FOREIGN PATENT DOCUMENTS

| | | |
|---|---|---|
| JP | 05-313071 A | 11/1993 |
| JP | 06-118307 A | 4/1994 |
| JP | 07-015721 A | 1/1995 |
| WO | WO 98/39728 | 9/1998 |
| WO | WO 98/44446 | 10/1998 |
| WO | WO 99/44062 A1 | 9/1999 |
| WO | WO 99/44063 A2 | 9/1999 |
| WO | WO 01/42796 A1 | 6/2001 |

OTHER PUBLICATIONS

"*The CAS 200™ Multiscan™ Automated Pathology Workstation*" by James V. Bacus, Compendium on the Computerized Cytology and Histology Laboratory, Tutorials of Cytology © 1994.

U.S. Appl. No. 60/075,979, filed Sep. 2, 1999, Kononen, et al.

U.S. Appl. No. 60/106,038, filed Sep. 2, 1999, Kallioniemi, et al.

U.S. Appl. No. 60/150,493, filed Sep. 19, 2002, Kallioniemi, et al.

U.S. Appl. No. 60/170,461, filed Jun. 14, 2001, Kallioniemi, et al.

(Continued)

*Primary Examiner*—Tom Y Lu (57) ABSTRACT

A method and apparatus for processing an image of a tissue sample microarray include placing a plurality of tissue samples in an array on a microscope slide. The tissue samples are then simultaneously and uniformly treated, as by staining. Images of the tissue making up the microarray are captured and stored together with identifying information related thereto. The images may be displayed from the digital storage medium using a programmed processor which can select various magnifications for display. The images also can be accessed by network and remotely.

OTHER PUBLICATIONS

U.S. Appl. No. 60/171,262, filed Jun. 14, 2001, Sauter, et al.

Barlund, M., et al., Detecting activation of ribosomal protein S6 kinase by complementary DNA and tissue microarray analysis. J Natl Cancer Inst, 2000. 92(15): p. 1252–9.

Barlund, M., et al., Multiple genes at 17q23 undergo amplification and overexpression in breast cancer. Cancer Res, 2000. 60(19): p. 5340–4.

Bowen, C., et al., Loss of NKX3.1 expression in human prostate cancers correlates with tumor progression. Cancer Res, 2000. 60(21): p. 6111–5.

Bucher, C. et al.. Automated High–Throughput Tissue Array Analysis for Assessing the Significance of HER–2 Involvement in Breast Cancer. ASCO Abstract 2388, 2000.

Bubendorf, L., et al., Survey of gene amplifications during prostate cancer progression by high–throughout fluorescence in situ hybridization on tissue microarrays. Cancer Res, 1999. 59(4): p. 803–6.

Bubendorf, L., et al., Hormone therapy failure in human prostate cancer: analysis by complementary DNA and tissue microarrays. J Natl Cancer Inst, 1999. 91(20): p. 1758–64.

Camp, R.L., L.A. Charette, and D.L. Rimm, Validation of tissue microarray technology in breast carcinoma. Lab Invest, 2000. 80(12): p. 1943–9.

Ingvarsson, S., et al., Reduced Fhit expression in sporadic and BRCA2–linked breast carcinomas. Cancer Res, 1999. 59(11): p. 2628–9.

Kononen, J., et al., Tissue microarrays for high–throughput molecular profiling of tumor specimens. Nat Med, 4: 844–847, 1998.

Kononen, J., Introduction to tissue array technology, Presented at the National Cancer Institute Working Group Meeting on Tissue Microarrays, Dec. 16–17, 1999.

Lee, S.K., et al., A nuclear factor, ASC–2, as a cancer–amplified transcriptional coactivator essential for ligand–dependent transactivation by nuclear receptors in vivo. J Biol Chem, 1999. 274(48): p. 34283–93.

Moch, H., et al., High–throughput tissue microarray analysis to evaluate genes uncovered by cDNA microarray screening in renal cell carcinoma. Am J Pathol, 1999. 154(4): p. 981–6.

Perrone, E.E., et al., Tissue microarray assessment of prostate cancer tumor proliferation in African—American and white men. J Natl Cancer Inst, 2000. 92(11): p. 937–9.

Richter, J., et al., High–throughput tissue microarray analysis of cyclin E gene amplification and overexpression in urinary bladder cancer. Am J Pathol, 2000. 157(3): p. 787–94.

Sallinen, S.L., et al., Identification of differentially expressed genes in human gliomas by DNA microarray and tissue chip techniques. Cancer Res, 2000. 60(23): p. 6617–22.

Schraml, P., et al., Tissue microarrays for gene amplification surveys in many different tumor types. Clin Cancer Res, 1999. 5(8): p. 1966–75.

Shah, R., Prostatic Hyperplasia of the Prostate Gland: Neoplastic Precursor or Innocent Bystander? Am J Pathol, 2001. 158(5): 1767–1773 (Presented at 2000 USCAP (Mar, New Orleans, LA) & the American Urological Association (May 2000, Atlanta, GA)).

Shibata, D. Pattern Recognition and Arrays: The Times Are A–Changing. Am J Pathol, 1999. 154(4): p. 979–80.

* cited by examiner

US 6,466,690 C1

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 6, line 66 to column 7, line 7:

In order to provide a magnification called for in *higher magnification capture*, the overall illumination and control of the microscope will be controlled so that the objective turret 142 will be rotated to place the higher power objective above the slide 18. The voltage to the lamp will be changed to adjust the lamp 168 to provide the proper illumination and color temperature as predetermined for the selected objective. The condenser diaphragm 176 will have its opening selected as appropriate to provide the proper illumination for that objective.

AS A RESULT OF REEXAMINATION, IT HAS BEEN DETERMINED THAT:

Claims 1–15 are cancelled.

New claims 16–32 are added and determined to be patentable.

16. *A method in accordance with claim 1 wherein the tissue sample images are microarray tissue sample dots, said method further comprising:*

*retrieving low magnification stored images of the tissue sample image signals and displaying them on an interactive display;*

*overlaying an exemplary grid of microarray tissue sample dot target center points over the tissue sample image dots; and*

*wherein the indexing comprises indexing the microarray tissue sample dots according to the overlay target center points for retrieving high magnification tissue sample dot images or portions thereof.*

17. *A method in accordance with claim 16 comprising:*

*defining a predetermined area about each tissue sample dot center point.*

18. *A method in accordance with claim 17 comprising:*

*providing a high magnification tissue sample dot specimen stored image which is size related to the predetermined area for each tissue sample dot.*

19. *A method in accordance with claim 18 wherein the providing of the high magnification specimen image comprises:*

*using the predetermined area on the low magnification image to scan the corresponding location on the specimen at higher magnification.*

20. *A method in accordance with claim 1 comprising:*

*retrieving low magnification stored images of the tissue sample image signals and displaying tissue sample images on an interactive image display screen to view a virtual tissue sample microarray corresponding to the array of tissue sample dots on the slide;*

*providing exemplary generated target center points for each of the microarray tissue sample dots from the displayed tissue sample images, the generated target center points being arranged in a row and column grid;*

*interactively relocating the generated target center points for those microarray tissue dots not in registration with the generated target center points for the tissue sample images; and*

*wherein the indexing comprises indexing for retrieval of high magnification specimen images according to the recentered target points.*

21. *A method in accordance with claim 1 comprising:*

*generating exemplary grid array target center points of the stored images of the tissue samples in the grid array;*

*comparing centers of the tissue samples to the exemplary target center points; and*

*recentering one or more target center points to bring it in registration with the center of the associated tissue sample; and*

*indexing the images of the tissue samples according to the target center points for image retrieval.*

22. *A method in accordance with claim 16 wherein the overlaying of the exemplary grid comprises:*

*identifying four corner points positioned near the centers of each of the four corners of the tissue sample images in the array; and*

*subsequently generating the exemplary grid using the four corners as a basis for the position of the exemplary grid on the specimen sample images.*

23. *A method in accordance with claim 16 comprising:*

*displaying the exemplary grid of target center points on the display of the low magnification tissue sample image dots; and*

*interactively recentering at least one of the target center points on the displayed tissue sample image dots.*

24. *A method in accordance with claim 21 wherein an operator compares the centers of low magnification images to target center points; and*

*recenters at least one target center point to a differently located target center point.*

25. *A method of processing an image of a tissue sample microarray having samples arrayed in a grid, comprising:*

*placing a plurality of tissue samples in a grid array on a microscope slide;*

*treating simultaneously all of the tissue samples on the slide with substantially identical treatment;*

*scanning each of the tissue samples to generate image signals representative thereof;*

*storing the tissue sample image signals;*

*displaying low magnification sample images in an interactive display of these images arranged in the grid;*

*overlaying an exemplary grid of microarray tissue sample target center points over the displayed low magnification tissue sample images in the grid array display;*

*using the sample target center points to locate points for extraction of high magnification tissue sample image signals to provide high magnification images of the respectively selected tissue sample; and*

*storing the high magnification images and indexing each of the higher magnification images of the tissue*

*samples according to the position of their respective low magnification images in the array for later retrieval and a display thereof.*

26. *A method in accordance with claim 25 comprising:*

*interactively recentering at least one target center point on the interactive display that is off-center relative to an adjacent, displayed tissue sample image;*

*extracting high magnification image signals at the recentered position of the recentered target center point.*

27. *A method in accordance with claim 26 comprising:*

*indexing a stored high magnification tissue sample image according to its recentered position.*

28. *A method in accordance with claim 26 wherein the extracting of the high magnification image signals comprises:*

*scanning a plurality of image tiles for each of the tissue samples in the low magnification grid array display of the tissue sample images to extract the high magnification image signals without scanning the empty spaces between image samples in the grid array display.*

29. *A method in accordance with claim 25 comprising:*

*commanding the extraction of successive high magnification images of successive centered and off-center tissue samples in the grid array display to proceed until high magnification images signals of all of the overlaid tissue samples are extracted.*

30. *A method in accordance with claim 25 wherein the indexing comprises:*

*associating a row and column position of the tissue sample on the displayed array grid of tissue sample images with respective stored higher magnification tissue sample images to identify the same for access by use of a row and column identifier.*

31. *A method in accordance with claim 30 comprising:*

*scanning and panning of adjacent image portions of the tissue sample into view.*

32. *A method in accordance with claim 25 comprising:*

*selecting a plurality of spaced corner points for the exemplary grid, each positioned near a center point of an associated tissue sample when overlaying the exemplary grid over an array low magnification tissue sample image.*

\* \* \* \* \*